(12) United States Patent
Zuehlsdorff et al.

(10) Patent No.: US 9,295,406 B2
(45) Date of Patent: Mar. 29, 2016

(54) AUTOMATIC OR SEMI-AUTOMATIC WHOLE BODY MR SCANNING SYSTEM

(75) Inventors: Sven Zuehlsdorff, Westmont, IL (US); Christopher Glielmi, Chicago, IL (US); Xiaoming Bi, Auroa, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 336 days.

(21) Appl. No.: 13/288,083

(22) Filed: Nov. 3, 2011

(65) Prior Publication Data

US 2012/0283546 A1 Nov. 8, 2012

Related U.S. Application Data

(60) Provisional application No. 61/482,682, filed on May 5, 2011.

(51) Int. Cl.
*A61B 5/055* (2006.01)
*A61B 6/00* (2006.01)

(52) U.S. Cl.
CPC ............... *A61B 5/055* (2013.01); *A61B 6/5217* (2013.01); *A61B 2503/12* (2013.01); *A61B 2505/00* (2013.01); *A61B 2576/00* (2013.01)

(58) Field of Classification Search
None
See application file for complete search history.

(56) References Cited

U.S. PATENT DOCUMENTS

| | | | | |
|---|---|---|---|---|
| 4,851,984 A * | 7/1989 | Doi et al. | | 382/108 |
| 4,912,050 A * | 3/1990 | Fossel | | 436/64 |
| 5,079,698 A * | 1/1992 | Grenier et al. | | 382/128 |
| 5,133,020 A * | 7/1992 | Giger et al. | | 382/128 |
| 5,172,419 A * | 12/1992 | Manian | | 382/132 |
| 5,213,101 A * | 5/1993 | Fossel | | 600/410 |
| 6,013,031 A * | 1/2000 | Mendlein et al. | | 600/442 |
| 6,301,378 B1 * | 10/2001 | Karssemeijer et al. | | 382/132 |
| 6,317,617 B1 * | 11/2001 | Gilhuijs et al. | | 600/408 |
| 6,476,607 B1 * | 11/2002 | Dannels et al. | | 324/309 |
| 6,794,869 B2 * | 9/2004 | Brittain | | 324/309 |
| 6,804,546 B1 * | 10/2004 | Thompson et al. | | 600/410 |
| 6,912,415 B2 * | 6/2005 | Kruger et al. | | 600/410 |
| 7,164,268 B2 * | 1/2007 | Mugler et al. | | 324/307 |

(Continued)

OTHER PUBLICATIONS

Brauck et al, "Feasibility of Whole-Body MR with T2 and T1 weighted Real-time Steady State Free Precession Sequences during Continuous Table Movement to Depict Metastases", Radiology, vol. 246: No. 3—Mar. 2008.*

(Continued)

*Primary Examiner* — Bo J Peng
(74) *Attorney, Agent, or Firm* — Peter R. Withstandley

(57) ABSTRACT

A system includes an image data processor for automatically processing data representing multiple patient anatomical images acquired in a single imaging scan. The images are acquired by, identifying multiple different anatomical elements in corresponding multiple different anatomical regions and identifying multiple different potentially pathology indicative features associated with the multiple different anatomical elements in response to first predetermined information associating different potentially pathology indicative features with corresponding different anatomical elements. The image data processor determines multiple different image acquisition methods for use in imaging the multiple different potentially pathology indicative features in response to second predetermined information associating different image acquisition methods with corresponding identified different pathology indicative features. An output processor collates images for output.

16 Claims, 9 Drawing Sheets

(56) References Cited

U.S. PATENT DOCUMENTS

| | | | |
|---|---|---|---|
| 7,251,520 B2 * | 7/2007 | Shankaranarayanan et al. | 600/415 |
| 7,272,251 B2 * | 9/2007 | Acar et al. | 382/128 |
| 7,308,126 B2 * | 12/2007 | Rogers et al. | 382/128 |
| 7,383,237 B2 * | 6/2008 | Zhang et al. | 706/20 |
| 7,519,209 B2 * | 4/2009 | Dawant et al. | 382/128 |
| 7,522,744 B2 * | 4/2009 | Bai et al. | 382/100 |
| 7,610,076 B2 | 10/2009 | Riederer et al. | |
| 7,792,778 B2 * | 9/2010 | Zhou et al. | 706/50 |
| 7,873,196 B2 * | 1/2011 | Henschke et al. | 382/128 |
| 7,876,939 B2 * | 1/2011 | Yankelevitz et al. | 382/128 |
| 7,899,225 B2 * | 3/2011 | Collins et al. | 382/128 |
| 7,983,732 B2 * | 7/2011 | Chen et al. | 600/407 |
| 8,000,510 B2 * | 8/2011 | Boeing et al. | 382/128 |
| 8,000,773 B2 * | 8/2011 | Rousso et al. | 600/436 |
| 8,014,576 B2 * | 9/2011 | Collins et al. | 382/128 |
| 8,131,044 B2 * | 3/2012 | Wollenweber et al. | 382/131 |
| 8,162,833 B2 * | 4/2012 | Zhang et al. | 600/437 |
| 8,175,351 B2 * | 5/2012 | Collins et al. | 382/128 |
| 8,184,882 B2 * | 5/2012 | Yu et al. | 382/128 |
| 8,195,275 B2 * | 6/2012 | Zwick et al. | 600/420 |
| 8,223,916 B2 * | 7/2012 | Srinivas et al. | 378/37 |
| 8,391,574 B2 * | 3/2013 | Collins et al. | 382/128 |
| 8,445,851 B2 * | 5/2013 | Rousso et al. | 250/363.04 |
| RE44,644 E * | 12/2013 | Mugler et al. | 324/307 |
| 2002/0102014 A1 * | 8/2002 | Ozaki et al. | 382/132 |
| 2003/0216637 A1 * | 11/2003 | Ho et al. | 600/415 |
| 2005/0010445 A1 * | 1/2005 | Krishnan et al. | 705/2 |
| 2005/0054910 A1 * | 3/2005 | Tremblay et al. | 600/411 |
| 2005/0171423 A1 * | 8/2005 | Ho et al. | 600/410 |
| 2005/0207631 A1 * | 9/2005 | Martens et al. | 382/131 |
| 2006/0018548 A1 * | 1/2006 | Chen et al. | 382/190 |
| 2007/0081706 A1 * | 4/2007 | Zhou et al. | 382/128 |
| 2007/0222442 A1 * | 9/2007 | Aldefeld et al. | 324/300 |
| 2008/0021301 A1 * | 1/2008 | Gonzalez et al. | 600/407 |
| 2008/0027889 A1 * | 1/2008 | Zhou et al. | 706/30 |
| 2008/0101665 A1 * | 5/2008 | Collins et al. | 382/128 |
| 2008/0294035 A1 * | 11/2008 | Zwick et al. | 600/420 |
| 2009/0177076 A1 * | 7/2009 | Aldefeld et al. | 600/410 |
| 2010/0040268 A1 * | 2/2010 | Boeing et al. | 382/128 |
| 2010/0191124 A1 * | 7/2010 | Prokoski | 600/473 |
| 2011/0112392 A1 | 5/2011 | Boernert et al. | |
| 2011/0184273 A1 | 7/2011 | Riederer | |
| 2014/0275966 A1 * | 9/2014 | Schwartz et al. | 600/411 |

OTHER PUBLICATIONS

Sadik et al, "Computer-Assisted Interpretation of Planar Whole-Body Bone Scans", The Journal of Nuclear Medicine, vol. 49, No. 12, Dec. 2008.*

Sommer et al, "Multicontrast Sequences with Continuous Table Motion: A Novel Acquisition Technique for Extended Field of View Imaging", Magnetic Resonance in Medicine 55: 918-922 (2006).*

Zenge et al, "Whole-Body Magnetic Resonance Imaging Featuring Moving Table Continuous Data Acquisition with High-Precision Position Feedback", Magnetic Resonance in Medicine 54:707-711 (2005).*

Body MRI Protocols, Department of Radiology, Geisel School of Medicine at Dartmouth University, Jun. 4, 2014.*

Saunders et al., Magnetic resonance imaging protocols for paediatric neuroradiology, Pediatr Radiol (2007) 37:789-797.*

D.G. Kruger, et al., "A dual-velocity acquisition method for continuously-moving-table contrast-enhanced MRA", Proc. Intl. Soc. Mag. Reson. Med. 11 (2004).

H.P. Fautz, "Sliding Multislice (SMS): A New Technique for Minimum FOV Usage in Axial Continuously Moving-Table Acquisitions" Magnetic Resonance in Medicine 55: 363-370 (2006).

Jor Barkhausen, et al., "Whole-Body MR Imaging in 30 Seconds with Real-Time True FISP and a Continuously Rolling Table Platform: Feasibility Study", Whole Body MR Imaging with Real-Time True FISP, vol. 220, No. 1, Radiology, Jul. 2001.

Peter Bornert, PhD and Bernd Aldefeld, PhD, "Principles of Whole-Body Continuously-Moving-Table MRI", Journal of Magnetic Resonance Imaging 28:1-12(2008).

M.O. Zenge, et al., "Quiescent-Interval Single-Shot Unenhanced Magnetic Resonance Angiographay featuring Continuous Table Movement", MR Applications Development, Siemens AG, Erlangen, Germany, Cardiovascular MR R&D, Siemens Healthcare, Chicago, IL, United States, Department of Radiology, NorthShore University HealthSystem Evanston, IL, United States.

Wikipedia, "Brain Tumor", web site content, printed Apr. 28, 2011, 10 pages.

Oliver Bruder, et al., "EuroCMR (European Cardiovascular Magnetic Resonance) Registry: Results of the German Pilot Phase", Journal of the American College of Cardiology, vol. 54, No. 15, 2009, online version of article, downloaded from content.onlinejacc.org by on Apr. 7, 2011.

Faisal Khosa, et al., "Prevalence of Noncardiac Findings on Clinical Cardiovascular MRI", American Journal of Roentgenology: 196, W380-W386, Apr. 2011.

Pamela K. Woodard, David A. Bluemke, Philip N. Cascade, J. Paul Finn, Arthur E. Stillman, Charles B. Higgins, Richard D. White, E. Kent Yucel, "ACR Practice Guideline for the Performance and Interpretation of Cardiac Magnetic Resonance Imaging (MRI)", Journal of the American College of Radiology, vol. 3, Issue 9, Sep. 2006, pp. 665-676.

Sandra Huff, et al., "Continuously Moving Table Time-of-Flight Angiography of the Peripheral Veins", Magnetic Resonance in Medicine 63: 1219-1229 (2010).

Florian M. Vogt, et al, "Peripheral Vascular Disease: Comparison of Continuous MR Angiography and Conventional MR Angiography—Pilot Study", Radiology, vol. 243: No. 1—Apr. 2007.

Patrick Asbach, et al, "Efficient Whole-Body MRI Interpretation: Evaluation of a Dedicated Software Prototype", Journal of Digital Imaging, vol. 21, Suppl 1, 2008: pp. S50-S58.

Robert D. Ambrosini, et al., "Computer-Aided Detection of Metastatic Brain Tumors Using Automated Three-Dimensional Template Matching", Journal of Magnetic Resonance Imaging 31:85-93 (2010).

American College of Radiology (ACR), "Magnetic Resonance Imaging (MRI)", web page http://www.acr.org/SecondaryMainMenuCategories/quality_safety/guidelins/mri.aspx, printed Apr. 7, 2011.

Peter H.B. McCreight, "ACR Practice Guideline for Performing and Interpreting Magnetic Resonance Imaging (MRI)", Journal of American College of Radiology, Revised 2006 (Res. 15 16g,34,35,36).

Elizabeth A. Morris, "ACR Practice Guideline for the Performance of Contrast-Enhanced Magnetic Resonance Imaging (MRI) of the Breast", Journal of American College of Radiology, Revised 2008 (res. 25).

THIEME EJournals, "Continuously Moving Table MRI in Oncology", Fortschr-Rontgenstr 2010; 182(11): 954-964.

Divyata Hingwala, et al, "Clinical utility of susceptibility-weighted imaging in vascular diseases of the brain", printed from web site http://www.neurologyindia.com on Apr. 29, 2011.

Philips, "MRI SmartExam", web site page http://www.healthcare.philips.com/main/products/mri/innovations/smartexam/index/wpd, printed on Apr. 7, 2011.

GE Healthcare, "MR Clinical Applications", web site http://www.gehealthcare.com/usen/mr/products/mrecho_cardiacimg.html, sprinted on Apr. 7, 2011.

Siemens Medical Solutions USA, Inc., "MAGNETOM Aera A Tim+Dot System", brochure Jan. 2011.

Co-pending U.S. Appl. No. 13/281,743, filed Oct. 26, 2011.

* cited by examiner

FIGURE 3

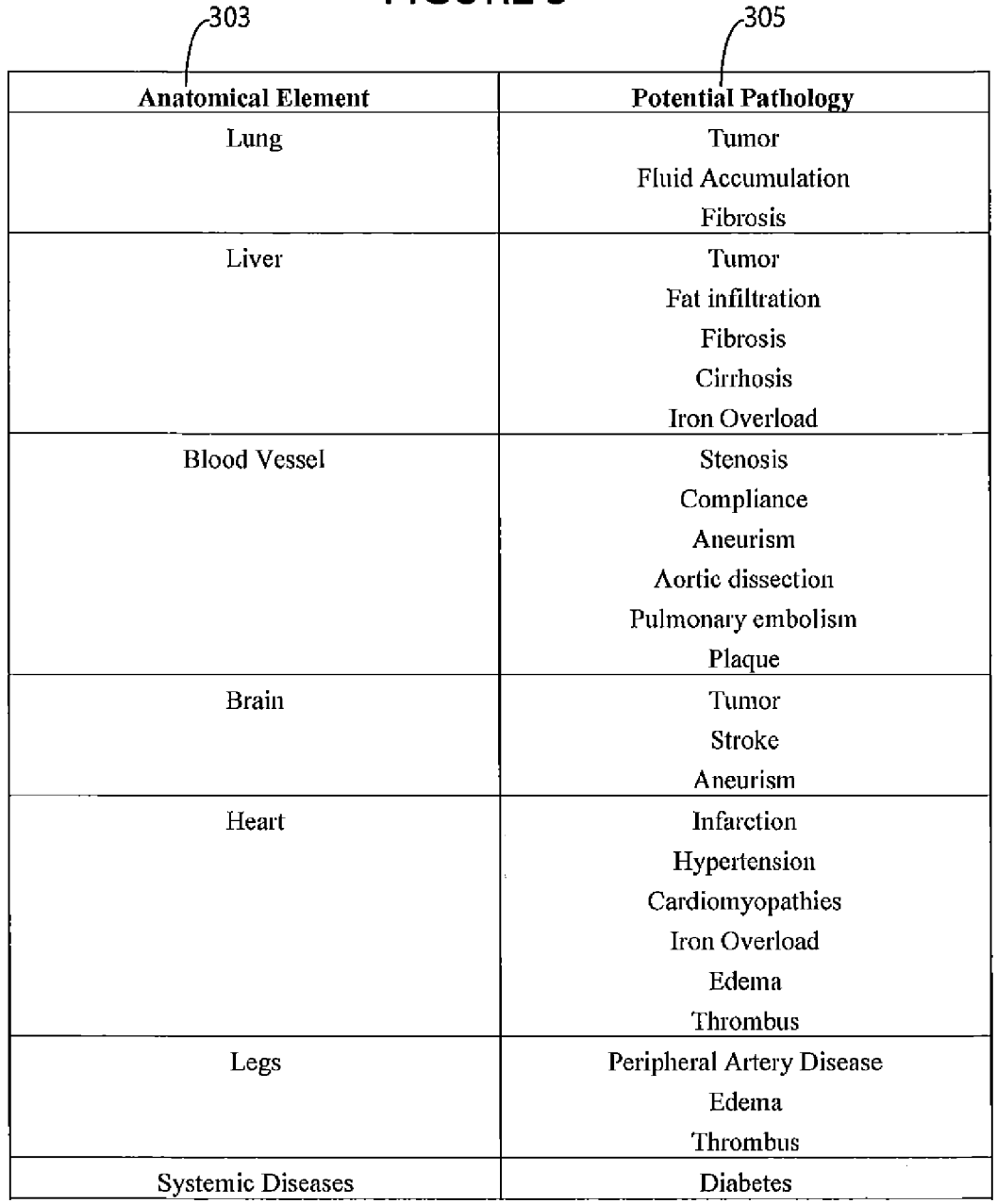

| Anatomical Element | Potential Pathology |
|---|---|
| Lung | Tumor |
| | Fluid Accumulation |
| | Fibrosis |
| Liver | Tumor |
| | Fat infiltration |
| | Fibrosis |
| | Cirrhosis |
| | Iron Overload |
| Blood Vessel | Stenosis |
| | Compliance |
| | Aneurism |
| | Aortic dissection |
| | Pulmonary embolism |
| | Plaque |
| Brain | Tumor |
| | Stroke |
| | Aneurism |
| Heart | Infarction |
| | Hypertension |
| | Cardiomyopathies |
| | Iron Overload |
| | Edema |
| | Thrombus |
| Legs | Peripheral Artery Disease |
| | Edema |
| | Thrombus |
| Systemic Diseases | Diabetes |

FIGURE 4

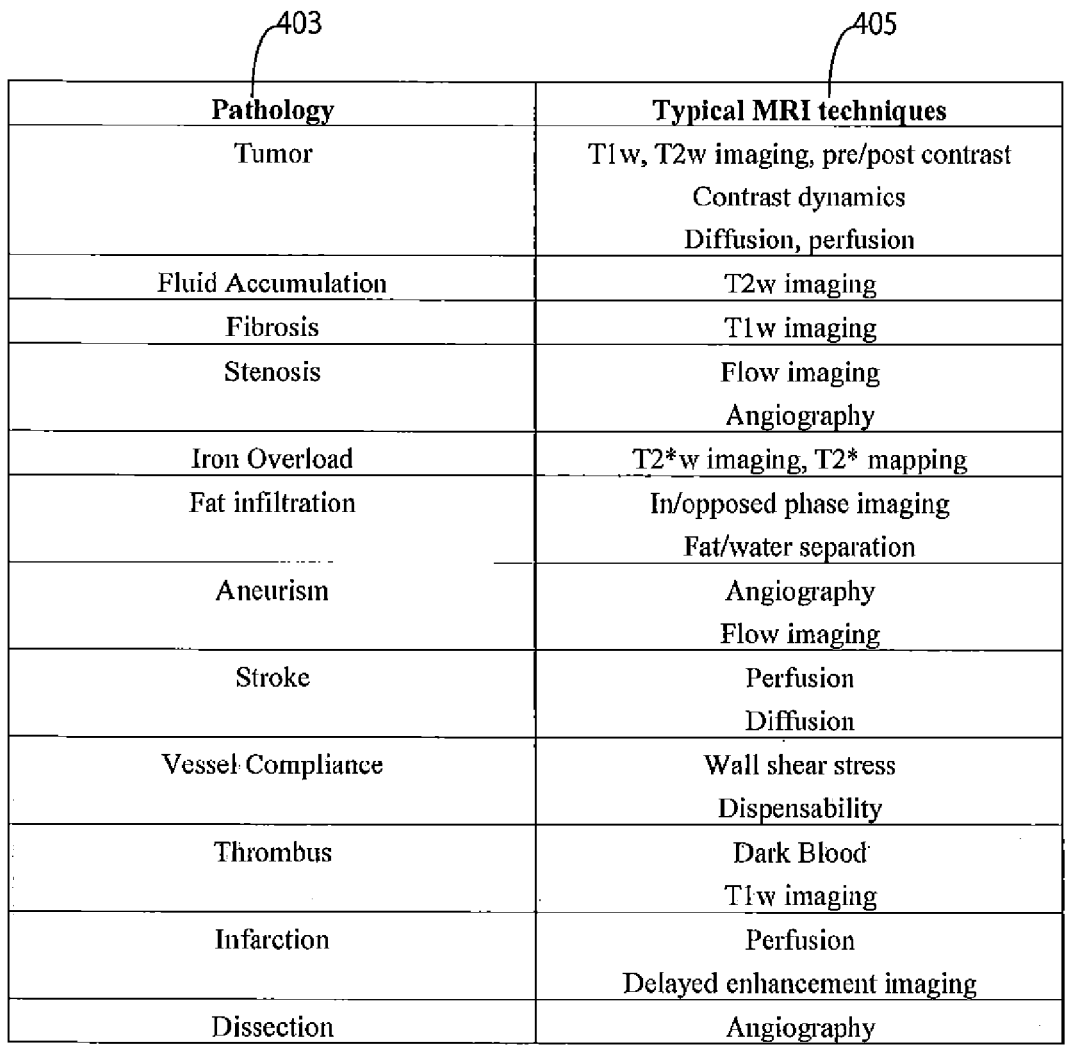

| Pathology | Typical MRI techniques |
|---|---|
| Tumor | T1w, T2w imaging, pre/post contrast<br>Contrast dynamics<br>Diffusion, perfusion |
| Fluid Accumulation | T2w imaging |
| Fibrosis | T1w imaging |
| Stenosis | Flow imaging<br>Angiography |
| Iron Overload | T2*w imaging, T2* mapping |
| Fat infiltration | In/opposed phase imaging<br>Fat/water separation |
| Aneurism | Angiography<br>Flow imaging |
| Stroke | Perfusion<br>Diffusion |
| Vessel Compliance | Wall shear stress<br>Dispensability |
| Thrombus | Dark Blood<br>T1w imaging |
| Infarction | Perfusion<br>Delayed enhancement imaging |
| Dissection | Angiography | ic data into an imaging session and optimizes MR imaging by
AUTOMATIC OR SEMI-AUTOMATIC WHOLE BODY MR SCANNING SYSTEM This is a non-provisional application of provisional application Ser. No. 61/482,682 filed 5 May, 2011, by S. Zuehlsdorff et al.

FIELD OF THE INVENTION

This invention concerns a system for imaging multiple anatomical regions of a patient by identifying multiple different potentially pathology indicative features and determining multiple different image acquisition methods for use in imaging multiple different potentially pathology indicative features of the regions.

BACKGROUND OF THE INVENTION

State of the art whole body MR screening systems often use a continuously moving patient support table during image data acquisition to collect images of an entire patient in an isocenter of an MRI scanner. Typical applications include screening for cancerous metastasis or MR angiographies with and without contrast media. However, continuous patient movement tends to generate a large amount of images that need be read and interpreted, typically through a labor intensive process, by a highly trained health care provider. Although there is dedicated software available to reduce the workload and shorten the reading time, such software is limited to research applications or specific clinical applications.

Known computer aided diagnostics (CAD) detect specific pathologies (e.g. metastatic tumors) to reduce reading time of a radiologist. However such pathology detection is typically performed as an image post-processing operation after a patient has stopped being scanned. A comprehensive and fully integrated system according to invention principles addresses the above deficiencies and lack of integration in existing whole body MR imaging and other applications.

SUMMARY OF THE INVENTION

An automatic or semi-automatic whole body MR scanning system combines screening, diagnostic scans and reporting. A system images multiple anatomical regions of a patient with multiple different potentially pathological anatomical regions in a single imaging scan. The system includes an image data processor for automatically processing data representing multiple patient anatomical images acquired in a single imaging scan. The images are acquired by, identifying multiple different anatomical elements in corresponding multiple different anatomical regions and identifying multiple different potentially pathology indicative features associated with the multiple different anatomical elements in response to first predetermined information associating different potentially pathology indicative features with corresponding different anatomical elements. The image data processor determines multiple different image acquisition methods for use in imaging the multiple different potentially pathology indicative features in response to second predetermined information associating different image acquisition methods with corresponding identified different pathology indicative features. An output processor collates images of multiple different potentially pathological features acquired using the associated corresponding different image acquisition methods into groups associated with the multiple different potentially pathological features for output.

BRIEF DESCRIPTION OF THE DRAWING

FIG. 3 shows a lookup table associating anatomical regions (e.g. organs) and potential pathology indicative features, according to invention principles.

FIG. 4 shows a lookup table associating different image acquisition methods with corresponding identified different pathology indicative features, according to invention principles.

DETAILED DESCRIPTION OF THE INVENTION

A comprehensive and fully integrated system according to invention principles integrates use of patient specific diagnostic data into an imaging session and optimizes MR imaging by minimizing risk of missing necessary diagnostic scans or rescheduling of patients for imaging. The system comprehensively combines MR screening, identification of pathology, diagnostic scans and reporting and reduces table and scan time of the patient as well as the risk of missing relevant diagnostic scans. The system also reduces dependency of image quality on operator experience. The system further streamlines reading and interpretation of images by providing guidance and automatically reporting relevant findings.

The system automatically identifies cancer patients with metastatic tumor growth regions for subsequent surgery or cancer staging and excludes certain pathologies to identify potential causes of patient symptoms. The system triggers relevant diagnostic image acquisition and reporting in response to incidental findings (e.g. an unexpected anomaly detected in a liver during a heart examination). A high prevalence of incidental findings has been reported in recent retrospective studies, including an analysis of 495 cardiac MRI studies revealing non-cardiac findings in 43% of cases. The system advantageously integrates a clinical workflow to specifically indentify and address incidental findings. Further, image acquisition volume of an intensive acquisition with small field of view (FOV, imaged anatomical area) capabilities (e.g. spectroscopy) is specified based on a localizing (e.g. anatomical) scan. Clinical findings in one scanning region are used to trigger acquisition in a related but separate anatomical region (e.g. abnormal ejection fraction from cardiac cine imaging triggers pulse wave velocity measurement in an aorta).

Figure 1:
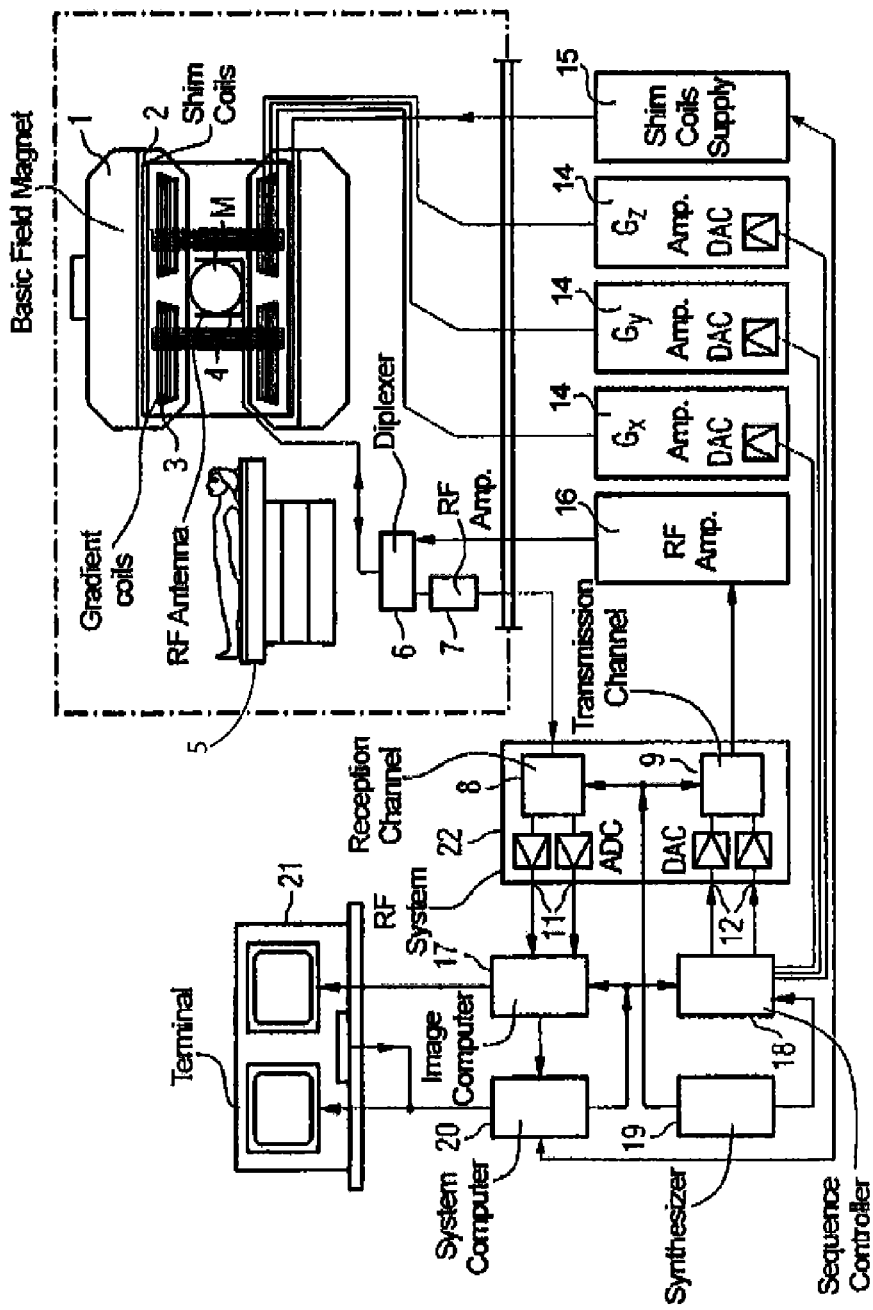
FIG. 1 shows a system for imaging multiple anatomical regions of a patient with multiple different potentially pathological anatomical regions in a single imaging scan, according to invention principles.

FIG. 1 shows system 10 for imaging multiple anatomical regions of a patient with multiple different potentially pathological anatomical regions in a single imaging scan. A basic field magnet 1 generates a strong magnetic field, which is constant in time, for the polarization or alignment of the nuclear spins in the examination region of an object, such as, for example, a part of a human body to be examined on automated movable patient support table 5. The automated patient support table 5 is controlled by system computer 20. The high homogeneity of the basic magnetic field required for the magnetic resonance measurement is provided in a spherical measurement volume M, for example, into which the parts of the human body to be examined are brought. In order to satisfy the homogeneity requirements and especially for the elimination of time-invariant influences, shim-plates made of ferromagnetic material are mounted at suitable positions. Time-variable influences are eliminated by shim coils 2, which are controlled by a shim-current supply 15.

Imaging computer 17 reconstructs an image from processed acquired RF echo pulse data. The processing of RF data, the image data and the control programs is performed under control of system computer 20. In response to predetermined pulse sequence control programs, sequence controller 18 controls generation of desired pulse sequences and corresponding scanning of k-space. In particular, sequence controller 18 controls the switching of the magnetic gradients at appropriate times, transmission of RF pulses with a determined phase and amplitude and reception of magnetic resonance signals in the form of RF echo data. Synthesizer 19 determines timing of operations of RF system 22 and sequence controller 18. The selection of appropriate control programs for generating an MR image and the display of the generated nuclear spin image is performed by a user via terminal (console) 21, which contains a keyboard and one or more screens.

The system 10 MR image acquisition device acquires imaging datasets comprising one or more image slabs individually comprising multiple image slices. An image data processor (in imaging computer 17) automatically processes data representing multiple patient anatomical images acquired in a single imaging scan by, identifying multiple different anatomical elements in corresponding multiple different anatomical regions. The image data processor identifies multiple different potentially pathology indicative features associated with the multiple different anatomical elements in response to first predetermined information associating different potentially pathology indicative features with corresponding different anatomical elements. The image data processor determines multiple different image acquisition methods for use in imaging the multiple different potentially pathology indicative features in response to second predetermined information associating different image acquisition methods with corresponding identified different pathology indicative features. An output processor in system computer 20 collates images of multiple different potentially pathological features acquired using the associated corresponding different image acquisition methods into groups associated with the multiple different potentially pathological features for output.

Figure 2:
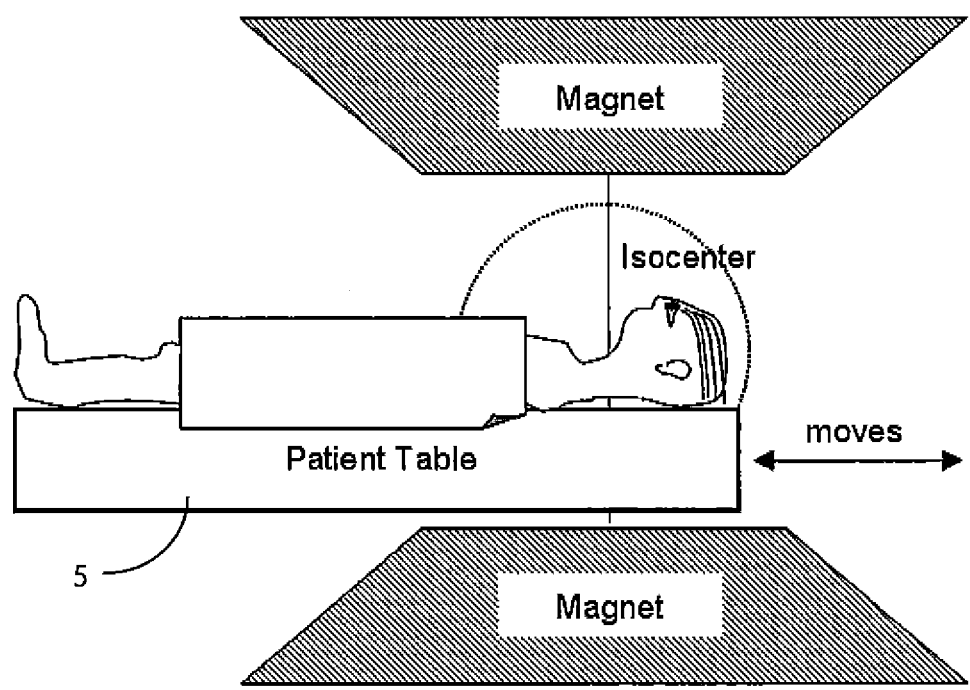
FIG. 2 shows a patient table system that automatically moves the patient into the isocenter of the scanner, according to invention principles.

FIG. 2 shows a patient table system that automatically moves the patient into the isocenter of the scanner. A patient support table controller in computer 20 (FIG. 1) automatically moves patient table 5 to isocenter of the imaging device to obtain images of the multiple different potentially pathological features in response to an identified one of the multiple different potentially pathology indicative features.

Figure 7:
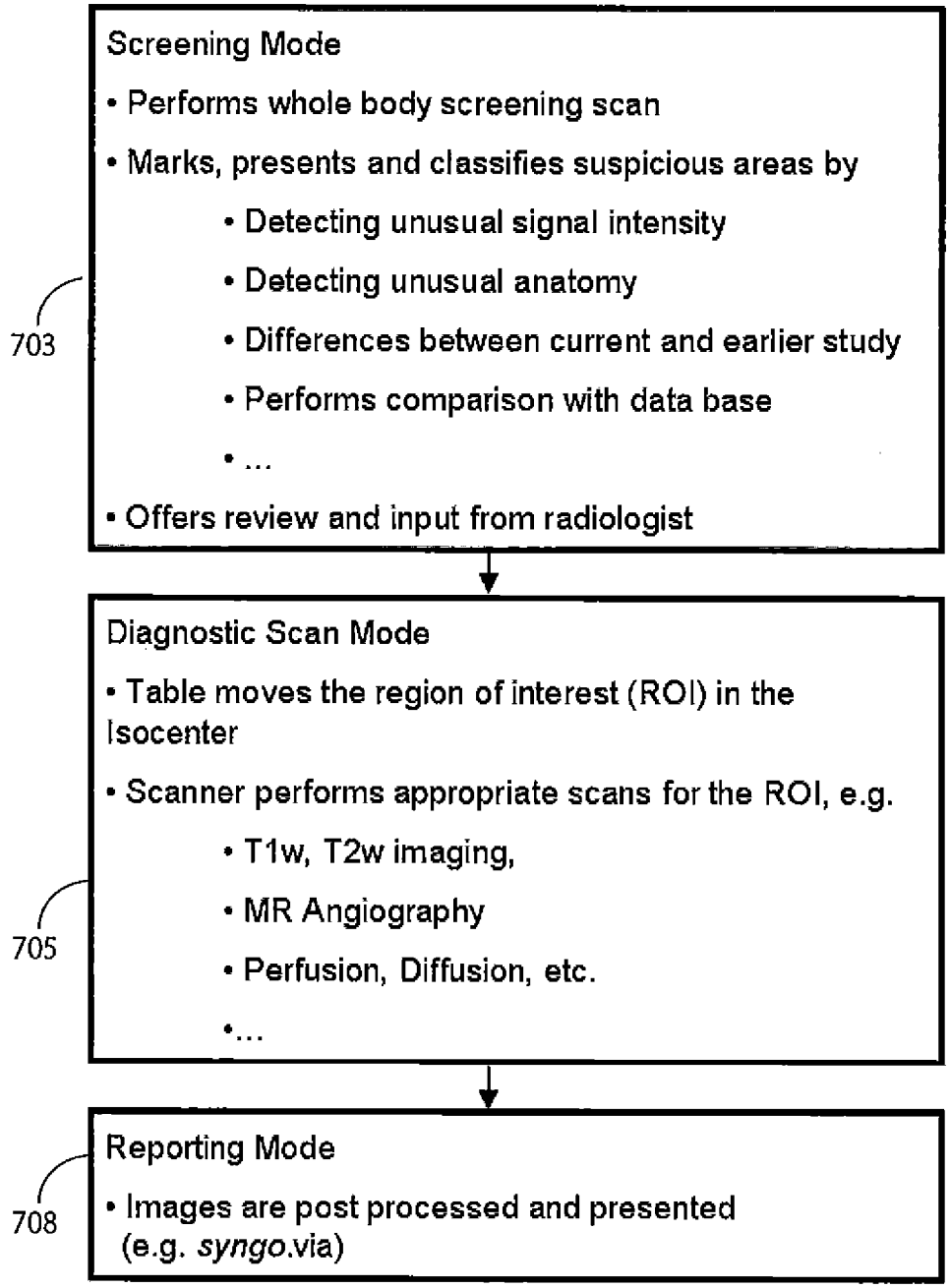
FIG. 7 shows steps employed by the system in a screening mode, diagnostic scan mode and reporting mode, according to invention principles.

FIG. 7 shows steps employed by the system in a screening mode, diagnostic scan mode and reporting mode. Comprehensive fully integrated system 10 (FIG. 1) does not limit whole body image reading methods to specific clinical applications. Specifically, during an initial screening mode in step 703, system 10 performs a whole body imaging scan in which suspected pathology is detected and pre-classified in automatic or semi-automatic fashion. Subsequently, in step 705 diagnostic scans are performed automatically using appropriate MR techniques for the suspected pathology. In step 708, the image data processor (in imaging computer 17) selects, sorts and presents relevant images in a post processing operation. The image data processor identifies, marks and classifies potentially pathological areas in an image by detecting unusual luminance intensity, unusual anatomy and differences between a currently acquired image and an image acquired on a previous occasion. The image data processor further compares detected anatomical features in an image with corresponding features in a database and presents the image and marked areas to a radiologist for review.

In the screening mode of step 703 the image data processor identifies regions of suspected pathology, in response to the MR scanner of system 10 performing a whole body scan (or scan of a portion of a body). As a typical patient is larger than the typical field-of-view (FOV) of commercially available scanners, the system continuously or stepwise moves patient table 5 into the isocenter of the scanner. The used imaging sequences are designed to show, anatomy, physiology, morphology and blood vessels as well as arterial-venous separation. In response to screening acquired images, the system identifies and classifies regions of potential pathological change. This is done in an automated, semi-automated or manual mode or in a combination of these modes. Manual identification involves a clinically established method in which a reading physician inspects images and identifies potential regions of interest. A computer aided diagnostics (CAD) application is used in an automatic or manually supervised screening process. The screening processes image data by performing segmentation of organs, e.g. heart, liver, kidney, brain, segmentation of organ tissue (e.g. white matter, gray matter), segmentation of blood vessels, separation of arteries and veins and assessment of blood vessel diameter and sharpness as well as classification of different tissue species (e.g. water, fat).

Subsequently, the image data processor automatically identifies potential regions of interest by (but not limited to) detecting unusual image luminance intensity, e.g., voids or bright spots in an organ or hyper-enhanced or hypo-enhanced signal representing an organ. The image data processor automatically identifies unusual anatomy, e.g. growth of tissue within an organ, abrupt change in blood vessel diameter or sharpness. The processor does this by detecting pixel luminance transitions demarcating object boundaries and as necessary, by comparison of detected objects with known template objects using transformation (scaling, rotation and translation) object matching operations. The processor also detects differences between a currently acquired image and a previously acquired image and compares detected findings with a database of normal findings. The image data processor initially classifies identified potential regions of interest using available information. In operation, the processor identifies a region of interest is normal, a low signal in T2w (T2 weighted) images of the liver potentially indicate iron overload, growth of tissue within an organ may potentially indicate a tumor and vessel anatomy may indicate a stenosis or other malformations, for example. This classification is subsequently used to determine an appropriate imaging method for each region with suspected pathology.

In the diagnostic mode of step 705 the MR scanner of system 10 automatically moves patient table 5 to position the anatomical region of interest (ROI) in the scanner isocenter and acquires appropriate diagnostic images for each region containing suspected pathology. The acquired images are advantageously comprehensive and appropriate for the areas being imaged and provide improved diagnostic quality that is operator independent and that are usable by health care providers with a limited level of expertise. The image data processor acquires diagnostic images corresponding to suspected pathology in response to medical guidelines, applicable standard of care and local physician preferences. Medical guidelines typically represent an expert consensus provided by societies such as the American College of Radiology (ACR) and include guidelines for cardiac and breast imaging, MR Angiography and perfusion and diffusion imaging, for example. Typically, for most suspected pathologies, an updated library is available that contains required clinical imaging protocols. A library (database) contains information indicating MRI protocols and required contrast, e.g. T1, T2 weighting, specific protocol parameters such as temporal, spatial resolution requirements, 2D, 3D, coverage as well as placement of saturation, inversion and fat bands.

In the diagnostic mode, the MR scanner of system 10 employs autoalignment methods e.g., autoalignment of head, knee as well as use of a contrast agent, respiratory gating, ECG trigger control and provides operator independent and high image quality acquisition according to guidelines. An imaging protocol library is automatically updated in response to change of detection guidelines and diagnostic scans are implemented in an automated and integrated manner so that non-specialist technicians are able to perform and supervise a scan without compromising diagnostic quality of resulting images. In response to the results of the screening phase, the system generates a list of regions of interest with suspected pathologies. Subsequently, the patient table automatically (or in response to user command) moves each region of interest into the iso-center and the system performs automatically or guided diagnostic scans until items on the list have been addressed and appropriate images have been collected in compliance with guidelines and local preferences.

In the reporting mode of step 708 the image data processor in a reporting mode processes and presents images to a reading physician. The acquisition of diagnostic images may result in multiple images showing different suspected pathologies. Depending on the nature of the images, post processing steps include calculation of maximum intensity images for use as angiographic images, reformatting 3D imaging data sets to comply with clinically relevant standard views of organs and generation of parameter maps. A display and reporting function provided by imaging computer 17 prepares and presents images in a clinically useful fashion for a specific pathology and provides a method to report findings e.g. via a findings navigator. System 10 advantageously provides a whole body examination and images in combination with a report to accelerate workflow. In a first step, images are sorted by body part. In another embodiment, images are prioritized by different criteria (e.g., clinical significance). Sorted images are presented in a clinical fashion that is appropriate for suspected pathology, until the findings are reported and a comprehensive report is generated.

Figure 8:
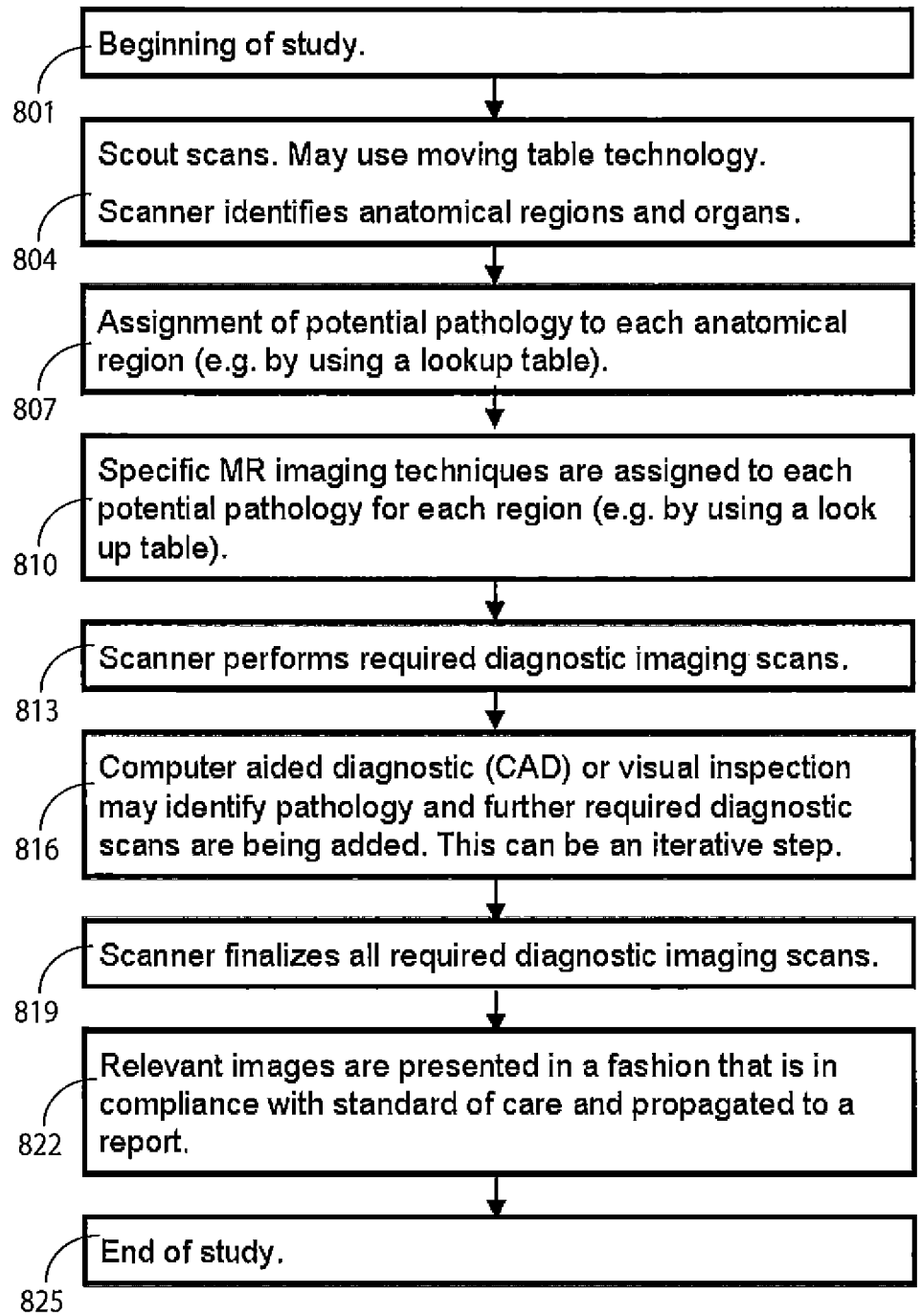
FIG. 8 shows a flowchart of a process performed by a system for acquiring diagnostic scans depending on body region (e.g. a specific organ) and potential pathology (e.g. tumor) to detect pathology and in response initiate subsequent additional imaging scans, according to invention principles.

FIG. 8 shows a flowchart of a process performed by a system for acquiring diagnostic scans depending on body region (e.g. a specific organ) and potential pathology (e.g. tumor) to detect pathology and in response initiate subsequent additional imaging scans. The FIG. 8 process comprises a study acquisition method using iterative steps that acquire diagnostic images in response to data identifying a body region (e.g. a specific organ), potential pathology (e.g. tumor), required scans and post processing to detect pathology and subsequent additional required scans. Relevant acquired images are presorted and presented in a report. Following the start of an imaging examination in step 801, system 10 in step 804 performs scout image acquisition scans and the image data processor (of computer 17) automatically processes data representing the acquired patient anatomical images by identifying different anatomical elements and different potentially pathology indicative features associated with the different anatomical elements. The image data processor identifies different anatomical elements and different potentially pathology indicative features by, detecting a transition in luminance data comprising an edge, determining a boundary of an item in response to a detected edge. The image data processor matches a shape of an item identified based on a determined boundary, with a template object associated with an element or pathology indicative feature derived from a repository, using scaling, translation and rotation operations to iteratively match the template object with the item.

The image data processor in step 807 assigns a potential pathology to the identified different anatomical elements using a lookup table associating anatomical regions (e.g. organs) and potential pathology indicative features, as illustrated in FIG. 3, for example. Specifically, FIG. 3 shows a lookup table including anatomical regions lung, liver, blood vessel, brain, heart, legs and systemic diseases in column 303 and associated corresponding potential pathology in column 305 such as tumor, fluid accumulation and fibrosis pathology being associated with a lung, for example. The image data processor in step 810 assigns one of multiple different image acquisition methods with a corresponding identified pathology indicative feature using a lookup table as illustrated in FIG. 4, for example.

FIG. 4 shows a lookup table associating different image acquisition methods with corresponding identified different pathology indicative features. The image data processor determines an image acquisition method for use in imaging a potentially pathology indicative feature in response to the lookup table associating different image acquisition methods with corresponding identified different pathology indicative features. In a further embodiment, the lookup table also associates pathology indicative features of a particular specific anatomical region or organ (not shown to preserve Figure clarity) with image acquisition methods. Pathology in column 403 is associated with imaging methods in column 405. The pathology of column 403 includes tumor, fluid accumulation, fibrosis, stenosis, iron overload, fat infiltration, aneurism, stroke, vessel compliance, thrombus, infarction and dissection, for example. MR imaging methods in column 405 that are associated with a tumor include T1 and T2 weighted imaging with pre-imaging and post-imaging contrast enhancement, contrast dynamic enhancement and diffusion and perfusion methods, for example. Further, some MRI methods are not usable for a particular pathology and some scans are conditional. For instance, delayed enhancement scans to detect infarction do not have to be performed if neither perfusion scan nor cine images show abnormalities. In this system, conditional diagnostic scans are conditional or are cascade scans comprising a sequence of imaging acquisition methods. In another embodiment, weighting is used in the table to indicate prevalence of pathology, risk factors (such as smoking), for example and to select a particular imaging method based on a weighted combination of identified pathology features.

Figure 5:
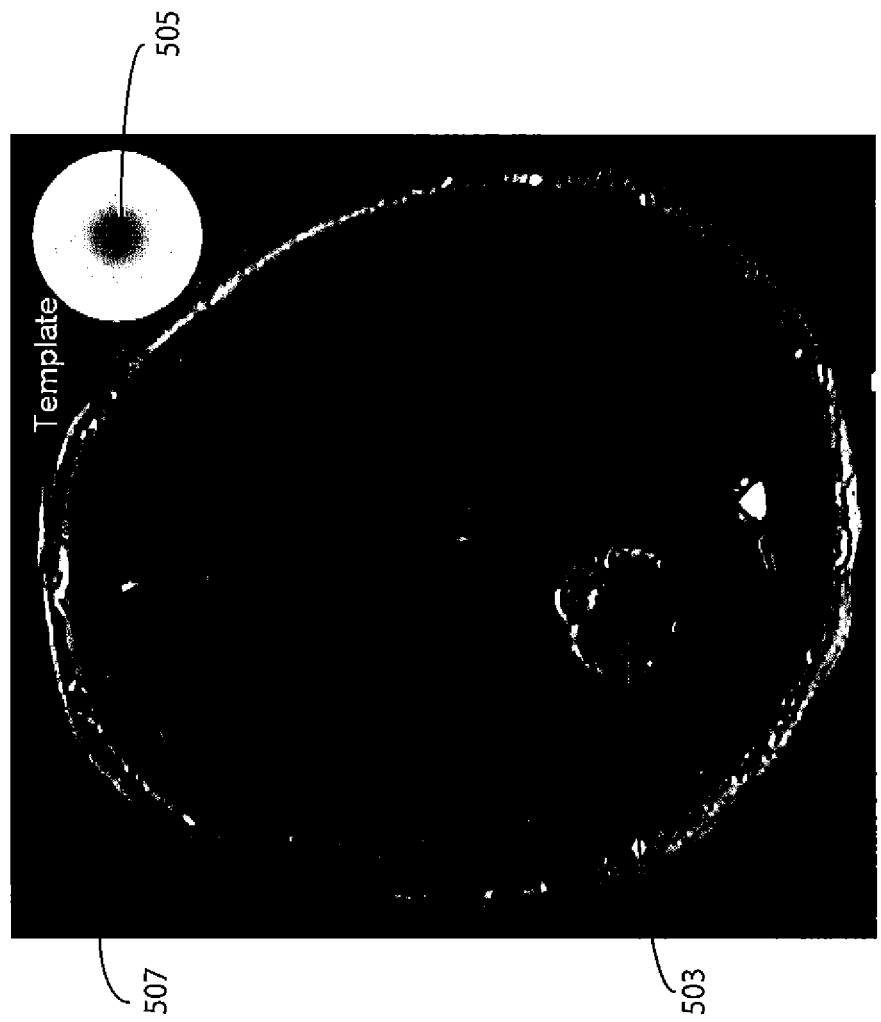
FIG. 5 shows a T1 weighted MRI image showing a brain tumor and a circular shaped template used for tumor identification, according to invention principles.

FIG. 5 shows a T1 weighted MRI image 507 showing a brain tumor and a circular shaped template 505 used by the image data processor for tumor 503 identification. Image 507 is acquired by system 10 using an automatically selected imaging method. Image 507 shows an example of a T1 weighted MR image after injection of contrast agent. The tumor accumulates contrast agent due to increased metabolism at the borders. In this case, a circular template matches the appearance (round shape, bright rim, darker core) and is used to identify the tumor.

Figure 6:
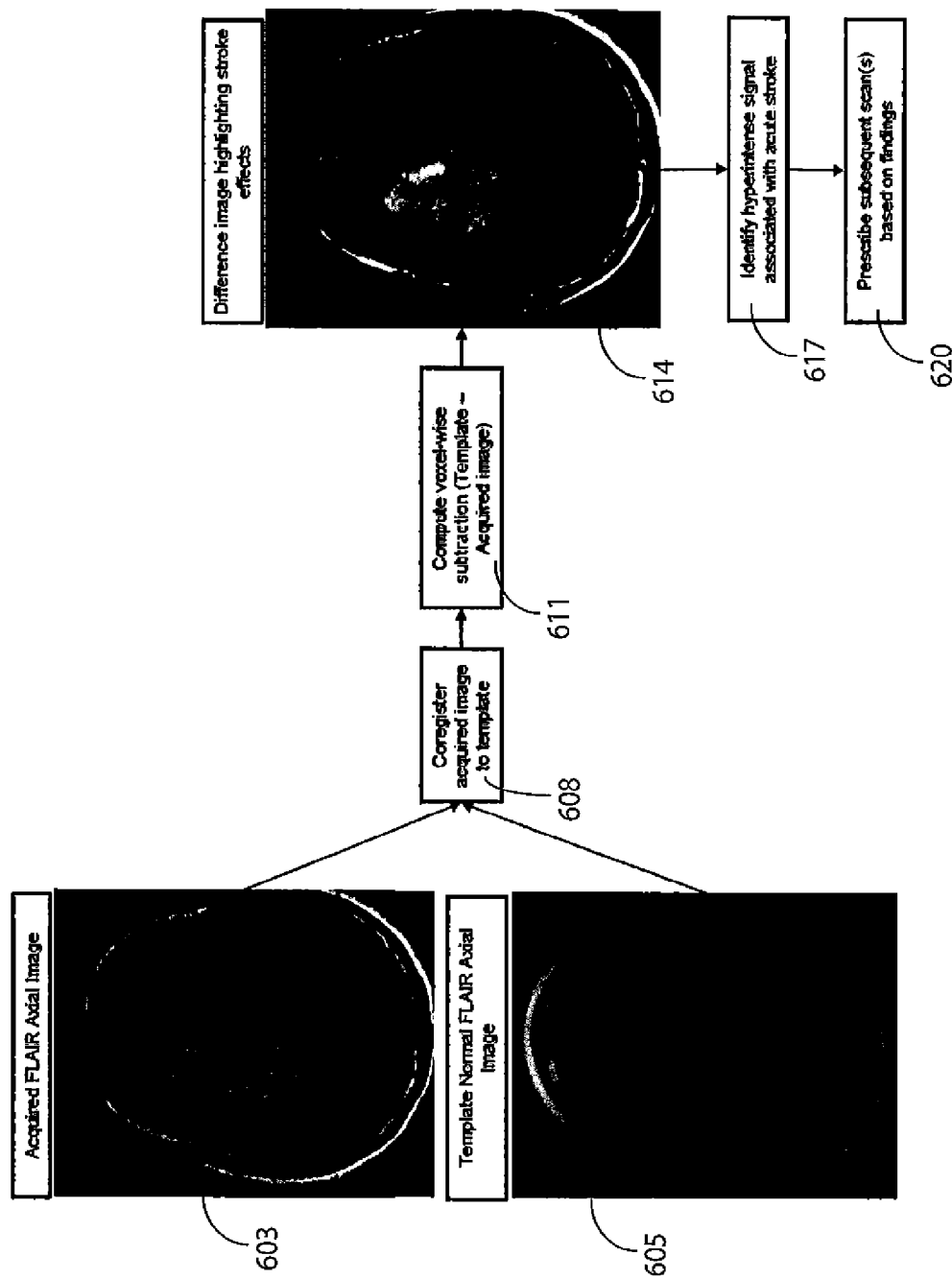
FIG. 6 shows a process for automatically detecting pathology by comparison with a normal template image, according to invention principles.

FIG. 6 shows a process for automatically detecting pathology by comparison with a normal template image. In one embodiment the image data processor automatically detects pathology in an acquired FLAIR (Fluid attenuated inversion recovery) axial image dataset representing image 603 with hyperintense signal due to acute stroke by comparison with a normal template image 605. Specifically, acute stroke effects are identified in image 603 by coregistration of image 603 with low resolution template image 605 with the same contrast in step 608. The template image is subtracted from the coregistered image to yield a difference image highlighting bright signal associated with pathology. Subtraction of these images in step 611 yields a hyperintense signal prominently displaying stroke effects in resultant difference image 614 and indicative of acute infarct. Image data processor in step 617 automatically identifies the hyperintense signal associated with stroke effects in image 614 using the image feature identification methods previously described.

Continuing with the process of FIG. 8, the image data processor in step 813 further uses a lookup table similar to the table of FIG. 4 in automatically initiating further diagnostic imaging scans (step 620 FIG. 6) using an imaging method selected from the lookup table in response to the detected stroke findings. In step 816, the image data processor automatically iteratively applies computer aided diagnostic analysis (and/or user manual review) to the diagnostic imaging scans of the stroke findings and finalizes and completes the scans in step 819. An output processor in computer 17 in step 822, collates images of multiple different potentially pathological features acquired using associated corresponding different image acquisition methods into groups associated the different potentially pathological features for output. Images are presented in a manner compatible with standard of care and included in a report. The imaging study terminates in step 825.

Figure 9:
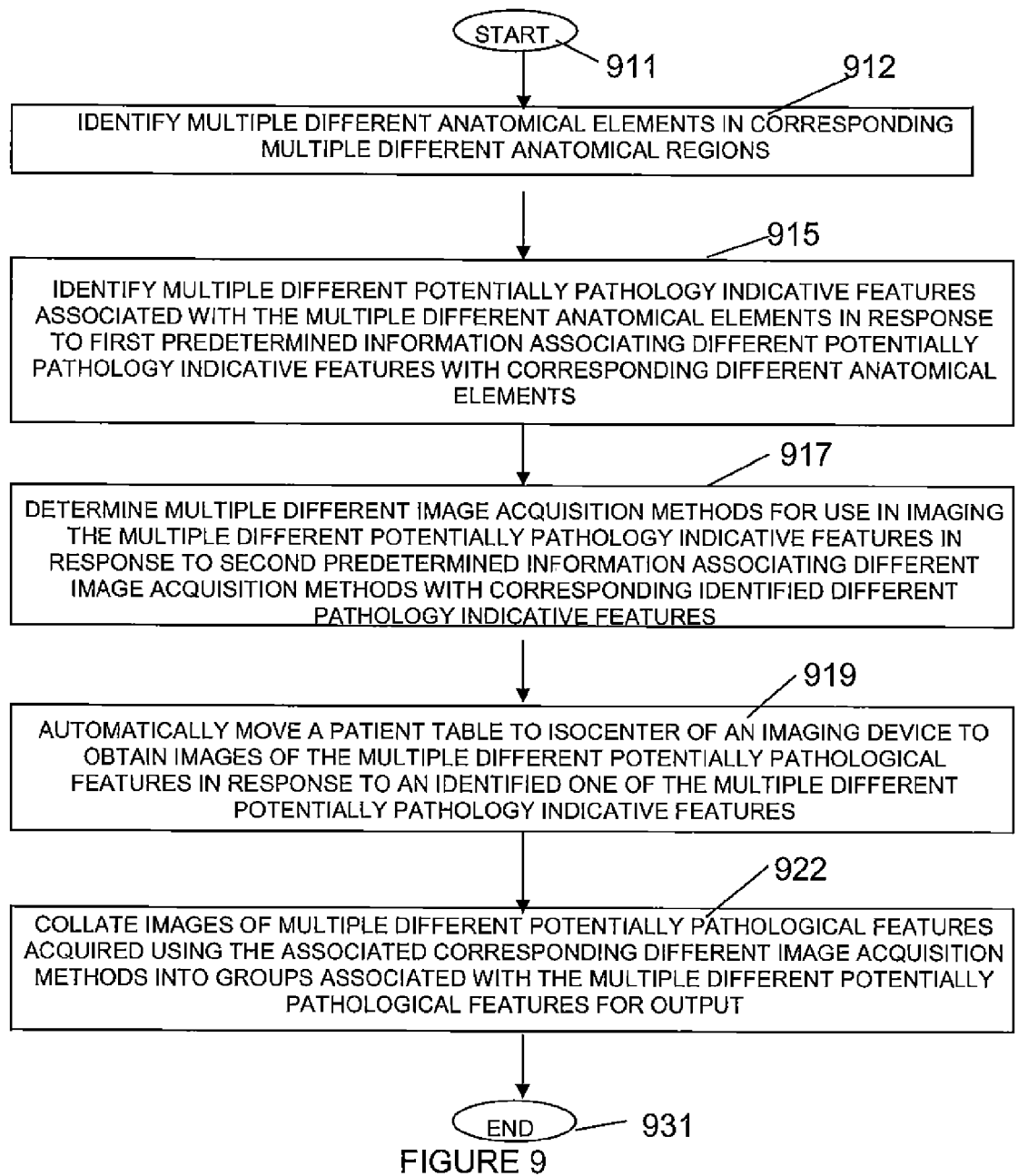
FIG. 9 shows a flowchart of a process performed by a system for imaging multiple anatomical regions of a patient with multiple different potentially pathological anatomical regions in a single imaging scan, according to invention principles.

FIG. 9 shows a flowchart of a process performed by system 10 for imaging multiple anatomical regions of a patient with multiple different potentially pathological anatomical regions in a single imaging scan such as a whole body scan. An image data processor (in imaging computer 17 FIG. 1) automatically processes data representing multiple patient anatomical images acquired in a single imaging scan. The image data processor in step 912 following the start at step 911 identifies multiple different anatomical elements in corresponding multiple different anatomical regions. The image data processor identifies the multiple different anatomical elements and the multiple different potentially pathology indicative features by, detecting a transition in luminance data comprising an edge, determining a boundary of an item in response to a detected edge, matching a shape of an item determined based on a determined boundary with a template object associated with an element or pathology indicative feature derived from a repository using scaling, translation and rotation operations to iteratively match a template object with an item. The multiple different anatomical elements comprise at least two of, (a) an organ, (b) a vessel, (c) tissue, (d) muscle, (e) bone, (f) fat and (g) fluid.

In step 915 the image data processor identifies multiple different potentially pathology indicative features comprising incidental findings associated with the multiple different anatomical elements in response to first predetermined information (e.g. lookup table of FIG. 3) associating different potentially pathology indicative features with corresponding different anatomical elements. The image data processor performs image feature segmentation and classifies a potentially pathology indicative feature. Specifically, the image data processor classifies a potentially pathology indicative feature in response to identifying at least one of, (a) vessel stenosis, (b) tissue growth in an organ, (c) low signal in a T2 weighted image of the liver, (d) a difference between a current image and an image of the same anatomical region obtained on an earlier occasion, (e) unusual signal luminance intensity representing an anomaly, (f) a change in blood vessel diameter and (g) a difference between an identified parameter of an image and a corresponding parameter of a normal population of patients sharing similar demographic characteristics. The demographic characteristics comprise at least one of age, weight, height, gender and pregnancy status.

The image data processor in step 917 determines multiple different image acquisition methods for use in imaging the multiple different potentially pathology indicative features in response to second predetermined information (e.g. the lookup table of FIG. 4) associating different image acquisition methods with corresponding identified different pathology indicative features. The second predetermined information associates different image acquisition methods with corresponding identified different pathology indicative features and with associated anatomical regions. In one embodiment, the image data processor determines an image acquisition method for imaging a first anatomical region in response to an identified potentially pathological feature of a different second anatomical region. The multiple different image acquisition methods comprise spectroscopy and MR methods indicating use of at least one of, (a) T1 weighting and (b) T2 weighting and methods indicating at least one of, temporal requirements, spatial requirements and inversion. The multiple different image acquisition methods comprise methods indicating use of at least two of, (a) a contrast agent, (b) ECG synchronization, (c) respiration synchronization, (d) an auto-alignment process and (e) 2D or 3D imaging.

In step 919 a patient support table controller (in system computer 20 FIG. 1) automatically moves a patient table to isocenter of an imaging device to obtain images of the multiple different potentially pathological features in response to identification of the multiple different potentially pathology indicative features. An output processor (in imaging computer 17) in step 922 collates images of multiple different potentially pathological features acquired using the associated corresponding different image acquisition methods, into groups associated with the multiple different potentially pathological features for output. The process of FIG. 9 terminates at step 931.

Returning to FIG. 1, in the basic magnetic field 1, a cylinder-shaped gradient coil system 3 is used, which consists of three windings, for example. Each winding is supplied with current by an amplifier 14 in order to generate a linear gradient field in the respective directions of the Cartesian coordinate system. The first winding of the gradient field system 3 generates a gradient $G_x$ in the x-direction, the second winding generates a gradient $G_y$ in the y-direction, and the third winding generates a gradient $G_z$ in the z-direction. Each amplifier 14 contains a digital-analog converter, which is controlled by a sequence controller 18 for the generation of gradient pulses at proper times.

Within the gradient field system 3, radio-frequency (RF) coils 4 are located which converts the radio-frequency pulses emitted by a radio-frequency power amplifier 16 via multiplexer 6 into a magnetic alternating field in order to excite the nuclei and align the nuclear spins of the object to be examined or the region of the object to be examined. In one embodiment, RF coils 4 comprise a subset or substantially all of, multiple RF coils arranged in sections along the length of volume M corresponding to the length of a patient. Further, an individual section RF coil of coils 4 comprises multiple RF coils providing RF image data that is used in parallel to generate a single MR image. RF pulse signals are applied to RF coils 4, which in response produces magnetic field pulses which rotate the spins of the protons in the imaged body by ninety degrees or by one hundred and eighty degrees for so-called "spin echo" imaging, or by angles less than or equal to 90 degrees for so-called "gradient echo" imaging. In response to the applied RF pulse signals, RF coils 4 receive MR signals, i.e., signals from the excited protons within the body as they return to an equilibrium position established by the static and gradient magnetic fields. The MR signals comprising nuclear spin echo signals received by RF coils 4 as an alternating field resulting from the precessing nuclear spins, are converted into a voltage that is supplied via an amplifier 7 and multiplexer 6 to a radio-frequency receiver processing unit 8 of a radio-frequency system 22.

The radio-frequency system 22 operates in an RF signal transmission mode to excite protons and in a receiving mode to process resulting RF echo signals. In transmission mode, system 22 transmits RF pulses via transmission channel 9 to initiate nuclear magnetic resonance in volume M. Specifically, system 22 processes respective RF echo pulses associated with a pulse sequence used by system computer 20 in conjunction with sequence controller 18 to provide a digitally represented numerical sequence of complex numbers. This numerical sequence is supplied as real and imaginary parts via digital-analog converter 12 in the high-frequency system 22 and from there to a transmission channel 9. In the transmission channel 9, the pulse sequences are modulated with a radio-frequency carrier signal, having a base frequency corresponding to the resonance frequency of the nuclear spins in the measurement volume M. The conversion from transmitting to receiving operation is done via a multiplexer 6. RF coils 4 emit RF pulses to excite nuclear proton spins in measurement volume M and acquire resultant RF echo signals. The correspondingly obtained magnetic resonance signals are demodulated in receiver processing unit 8 of RF system 22 in a phase-sensitive manner, and are converted via respective analog-digital converters 11 into a real part and an imaginary part of the measurement signal and processed by imaging computer 17.

DEFINITIONS

A single imaging scan comprises an automated image acquisition process for acquiring a sequence of images using an imaging system that is performed according to predetermined instruction and without human intervention.

An inversion recovery (IR) pulse inverts longitudinal magnetization from the positive z-axis by 180 degrees to the negative z-axis. IR pulses are used as preparation pulses prior to a main imaging pulse sequence to achieve different kinds of MR contrast (such as T1 weighted, T2 weighted). Adiabatic IR pulses are used to give more uniform contrast throughout an imaging volume than non-adiabatic RF pulses.

iPAT (integrated Parallel Acquisition Techniques) comprises "parallel imaging". It enables faster scanning through reduced phase encoding and addition of RF coil information. An iPAT factor of 2 enables scanning about twice as fast, iPAT factor of 3 enables scanning about three times as fast and so on.

TI comprises inversion time, the time between an inversion recovery pulse and the next RF excitation pulse. TI determines the image contrast.

$T_1$ comprises the longitudinal (or spin-lattice) relaxation time $T_1$ decay constant.

$T_2$ comprises the transverse (or spin-spin) relaxation time $T_2$ is the decay constant for a proton spin component.

TR comprises repetition time, the time between successive RF excitation pulses.

A saturation pulse (or saturation recovery pulse) comprises an RF pulse, typically 90 degrees (or any odd multiple of 90 degrees). Some systems use a spoiler gradient after the RF pulse. In a particular type of partial saturation pulse sequence a preceding pulse leaves the spins in a state of saturation, so that recovery at the time of the next pulse has taken place from an initial condition of no magnetization.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouth, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-9 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A system initiates diagnostic image acquisition of a body region in response to automatic detection of incidental findings in an image detected of a different body region (e.g. an unexpected anomaly detected in a liver during a heart examination). Further, the system and processes may, in alternative embodiments, be located on one or more (e.g., distributed) processing devices on a network linking the units of FIG. 1. Any of the functions and steps provided in FIGS. 1-9 may be implemented in hardware, software or a combination of both.

What is claimed is:

1. An image processing system comprising:
a medical imaging device having a patient support table;
a database comprising:
   (i) first lookup information associating descriptions of a plurality of predetermined anatomical elements and a plurality of predetermined potential pathologies, each of the plurality of predetermined anatomical elements being associated with one or more of the plurality of predetermined potential pathologies; and
   (ii) second lookup information associating the plurality of predetermined potential pathologies and a plurality of predetermined image acquisition methods, each of the plurality of predetermined potential pathologies being associated with one or more of the plurality of predetermined image acquisition methods;
a repository comprising a template image comprising a plurality of template objects corresponding to a plurality of previously acquired anatomical elements;
an image data processor configured to automatically process data representing a plurality of patient anatomical images acquired from the medical imaging device by:
   identifying: (i) a plurality of different anatomical elements of a patient in a corresponding plurality of different anatomical regions of the patient; and (ii) a plurality of different potentially pathological indicative features associated with said plurality of different anatomical elements of the patient by detecting a transition in luminance intensity between the portions of the plurality of patient anatomical images depicting the plurality of different anatomical elements of the patient and portions of the template image depicting the plurality of previously acquired anatomical elements; and
   assigning one or more of the potential pathologies in the first lookup information to the identified plurality of different anatomical elements of the patient using the association of each of the plurality of predetermined anatomical elements with the one or more predetermined potential pathologies in the first lookup information; and assigning one or more of the plurality of predetermined image acquisition methods in the second lookup information to the one or more assigned potential pathologies in the first lookup information using the association of each of the plurality of predetermined potential pathologies with the one or more predetermined image acquisition methods in the second lookup information;
an output processor configured to collate one or more images depicting said identified plurality of different potentially pathological indicative features acquired by the medical imaging device using the one or more assigned predetermined image acquisition methods; and
a patient support table controller configured to automatically move the patient support table to isocenter of the medical imaging device to obtain the one or more images depicting said plurality of different potentially pathological indicative features in response to an identified one of said plurality of different potentially pathological indicative features.

2. A system according to claim 1, wherein
said image data processor is further configured to assign one or more of the plurality of predetermined image acquisition methods for imaging a first anatomical region in response to an identified potentially pathological indicative feature of a different second anatomical region.

3. A system according to claim 1, wherein
said plurality of patient anatomical images acquired by the medical imaging device is acquired using a single imaging scan comprising a whole body scan.

4. A system according to claim 1, wherein
said plurality of different potentially pathological indicative features comprises incidental findings.

5. A system according to claim 1, wherein
said plurality of predetermined image acquisition methods comprises spectroscopy.

6. A system according to claim 1, wherein
said plurality of predetermined image acquisition methods comprises magnetic resonance imaging methods indicating use of at least one of: (a) T1 weighting and (b) T2 weighting.

7. A system according to claim 1, wherein
said plurality of predetermined image acquisition methods comprise methods indicating use of at least two of: (a) a contrast agent, (b) ECG synchronization, (c) respiration synchronization, (d) an auto-alignment process and (e) 2D or 3D imaging.

8. A system according to claim 1, wherein
said plurality of predetermined image acquisition methods comprises MR methods indicating at least one of: (a) temporal requirements, (b) spatial requirements and (c) inversion.

9. A system according to claim 1, wherein
said image data processor is configured to classify one of said plurality of different potentially pathological indicative features in response to identifying at least one of: (a) vessel stenosis, (b) tissue growth in an organ and (c) low signal in a T2 weighted image of the liver.

10. A system according to claim 1, wherein
said image data processor is configured to classify one of said plurality of different potentially pathological indicative features in response to identifying a difference between a current image and an image of the same anatomical region obtained on an earlier occasion.

11. A system according to claim 1, wherein
said image data processor is configured to classify one of said plurality of different potentially pathological indicative features in response to identifying a difference between an identified parameter of an image and a corresponding parameter of a normal population of patients sharing similar demographic characteristics.

12. A system according to claim 11, wherein
said demographic characteristics comprise at least one of age, weight, height, gender, and pregnancy status.

13. A system according to claim 1, wherein
said plurality of different anatomical elements of the patient comprises at least two of: (a) an organ, (b) a vessel, (c) tissue, (d) muscle, (e) bone, (f) fat and (g) fluid.

14. A system according to claim 1, wherein
said image data processor is further configured to identify said plurality of different anatomical elements of the patient and said plurality of different potentially pathological indicative features by:
  detecting the transition in luminance intensity of data comprising an edge,
  determining a boundary of an item in response to the detected edge, and
  matching a shape of the item with a shape of a template object of the template image based on a determined boundary with the template object associated with one or more of the previously acquired anatomical elements or pathological indicative features derived from the repository using scaling, translation and rotation operations to iteratively match a template object with an item.

15. An image processing system comprising:
a medical imaging device having a patient support table;
a database comprising:
  (i) first lookup information associating descriptions of a plurality of predetermined anatomical elements and a plurality of predetermined potential pathologies, each of the plurality of predetermined anatomical elements being associated with one or more of the plurality of predetermined potential pathologies; and
  (ii) second lookup information having the plurality of predetermined potential pathologies and a plurality of predetermined image acquisition methods, each of the plurality of predetermined potential pathologies being associated with one or more of the plurality of predetermined image acquisition methods;

an image data processor configured to automatically process data representing a plurality of patient anatomical images acquired from the medical imaging device by:
  identifying:
    (i) a plurality of different anatomical elements of a patient in a corresponding plurality of different anatomical regions of the patient; and
    (ii) a plurality of different potentially pathology indicative features associated with said plurality of different anatomical elements using first predetermined information associating different potentially pathology indicative features with corresponding different anatomical elements;
  assigning one or more of the potential pathologies in the first lookup information to the identified plurality of different anatomical elements of the patient using the association of each of the plurality of predetermined anatomical elements with the one or more predetermined potential pathologies in the first lookup information; and
  assigning one or more of the plurality of predetermined image acquisition methods in the second lookup information to the one or more assigned potential pathologies in the first lookup information using the association of each of the plurality of predetermined potential pathologies with the one or more predetermined image acquisition methods in the second lookup information;
an output processor configured to collate one or more images depicting said identified plurality of different potentially pathological indicative features acquired by the medical imaging device using the one or more assigned predetermined image acquisition methods; and
a patient support table controller configured to automatically move the patient support table to isocenter of the medical imaging device to obtain the one or more images depicting said plurality of different potentially pathological indicative features in response to an identified one of said plurality of different potentially pathological indicative features.

16. A system according to claim 15, further comprising a repository comprising a plurality of template objects corresponding to a plurality of previously acquired anatomical elements of a template image:
  wherein the image data processor is further configured to identify the plurality of different anatomical elements of the patient and the plurality of different potentially pathological indicative features associated with said plurality of different anatomical elements by detecting a transition in luminance intensity between portions of the plurality of patient anatomical images acquired by the medical imaging device depicting the acquired plurality of different anatomical elements of the patient and portions of the template image depicting the plurality of previously acquired anatomical elements.

* * * * *